United States Patent
Matilainen et al.

[11] Patent Number: 6,037,184
[45] Date of Patent: Mar. 14, 2000

[54] METHOD AND APPARATUS FOR TAKING SAMPLE

[75] Inventors: Kari Matilainen, Porvoo; Ari Palmroos, Kerava; Auli Nummila-Pakarinen, Porvoo; Markku Savolainen, Kulloo; Timo Blomqvist, Porvoo, all of Finland; Jouni Takakarhu, Lyngby, Denmark; Klaus Nyfors, Porvoo, Finland

[73] Assignee: Borealis Polymers OY, Porvoo, Finland

[21] Appl. No.: 08/952,371

[22] PCT Filed: May 13, 1996

[86] PCT No.: PCT/FI96/00270

§ 371 Date: Nov. 10, 1997

§ 102(e) Date: Nov. 10, 1997

[87] PCT Pub. No.: WO96/35936

PCT Pub. Date: Nov. 14, 1996

[30] Foreign Application Priority Data

May 11, 1995 [FI] Finland ..................................... 952301

[51] Int. Cl.$^7$ ....................................................... G01N 1/20
[52] U.S. Cl. .................. 436/177; 73/863.81; 73/864.81; 422/101; 422/119; 422/131; 422/132; 436/178; 436/181; 526/59; 526/64
[58] Field of Search ..................................... 422/101, 119, 422/131, 132; 436/177, 178, 181; 73/863.81, 864.81; 526/59, 64

[56] References Cited

U.S. PATENT DOCUMENTS

| | | |
|---|---|---|
| 3,556,730 | 1/1971 | Mitacek . |
| 4,112,768 | 9/1978 | Holland et al. . |
| 4,469,853 | 9/1984 | Mori . |
| 5,149,658 | 9/1992 | Cassaday et al. . |
| 5,180,558 | 1/1993 | Takakarhu .............................. 422/131 |
| 5,252,218 | 10/1993 | Muraldihara et al. .................. 210/636 |
| 5,602,348 | 2/1997 | Takakarhu et al. .................. 73/864.81 |

FOREIGN PATENT DOCUMENTS

| | | |
|---|---|---|
| 0455333 | 11/1991 | European Pat. Off. . |
| 95319 | 11/1994 | Finland . |
| 9427134 | 11/1994 | WIPO . |

*Primary Examiner*—Jan Ludlow
*Attorney, Agent, or Firm*—Steinberg & Raskin, P.C.

[57] ABSTRACT

A method and apparatus for taking a sample from a flowing suspension formed by polymer particles and hydrocarbon diluent in a olefin polymerization process including at least one filter situated at a plane of an inside surface of a transfer conduit between reactors. Each filter includes perforations or pores having a size to prevent substantially any of the catalyst used in the polymerization process from passing through the filter, e.g., smaller than the smallest particle size of a catalyst used in the polymerization process. The pore or perforation size of each filter is preferably 0.1–10 μm, preferably between 0.2–1 μm. A pressure difference permits at least partial vaporization of the sample as it passes through the filter.

12 Claims, 2 Drawing Sheets

METHOD AND APPARATUS FOR TAKING SAMPLE

FIELD OF THE INVENTION

The invention concerns a method and an apparatus for taking a sample in slurry polymerization.

BACKGROUND OF THE INVENTION

It has been developed various method for manufacturing solid and semisolid polymers from hydrocarbons, for example 1-olefins. In one such method olefins, like ethylene, propylene, butene and pentenes are polymerized in the presence of catalysts in hydrocarbon diluents or in reaction medium formed by monomers. Hereby the reactants are kept in liquid phase or in supercritical pressure by maintaining a sufficient pressure in the polymerization reactor. When the forming polymer is insoluble or slightly soluble in said medium, the polymers forms as particles and both the reaction medium moving in the reactor and the product flow comprise a suspension formed by polymer particles, medium and monomers. The product flow is introduced usually to a separation vessel of polymer, where solids and liquid and gaseous substances are separated from each other.

One reactor type applied such methods is a tube reactor forming a continuous loop, where polymerization takes place in the turbulent flow circulating in the loop reactor. Polymer, diluents and monomers are taken out from the loop reactor either continuously or periodically via a discharge valve and are introduced into a separator, where polymer is separated by lowering pressure.

In order to control the polymerization reaction samples can be taken from the product flow of the reactor either continuously or periodically. The typical way is to take a sample from a gas flow coming out from the polymer separation tank and to analyze this gas sample by various methods, for example by gas chromatography. Such an arrangement is disclosed for example in U.S. Pat. No. 3,556,730.

In this known procedure, the period of delay that occurs from the departure of the product from the polymerization reactor until the time of start of the analysis is often considerably long and during that period essential chances may take place in the process. Thus the sample is not representative. That is why it would be desirable to make said period of delay in the analysis shorter.

In Finnish patent 85191, a method is disclosed by which essential shortening of the sampling delay is achieved. In this method, the sample is taken from the product pipe via an on/off-type shut valve, which is closed for the time of pressure surge produced on opening the discharge valve, and which valve is opened after pressure surge.

The control of polymer properties in slurry polymerization requires a precise control of concentrations. The control is carried out conventionally by analyzing feed concentrations or concentrations of gas phase separated from the product. These measurements do not give precise information from liquid phase concentrations in the reactor at certain moment.

When feed concentrations are analyzed, the real concentrations in the reactor are not known. When gas phase concentrations in a stirred-tank reactor are analyzed, the real liquid phase concentrations are not known. Further, problems are produced by the adhering of polymer particles in sample take-out system. When sample take-out takes place from the gas flow after the product pipe of the reactor (after the separation tank), the adhering of polymer particles in the sampling line causes problems. Further, possible return-blow gases in the product filters can disturb the analysis and there may be a long time delay until the concentration measurement has been carried out. Additionally, the analyzing from the gas phase is impossible, if the polymerization suspension is fed from one reactor to another without separation of gases. Analyzing straight from the slurry by using a conventional filter is not possible, because the filter is under reaction conditions and, if small catalyst particles remains on the face of the filter, said particles continue polymerization on the filter and plug it rapidly.

In Finnish patent application FI932159. a method for taking sample straight from the liquid phase of a loop reactor is disclosed. An in-line filter placed in the flow pipe attached to a loop reactor is applied in the method. The one end of said flow pipe is connected to the suction side of loop circulation pump and the other end is connected to the pressure side of the pump. The pump causes a high-speed flow, by which the filter surface inside the pipe is tried to keep clean.

In the method according this publication, the sample is taken out from the product suspension circulating in loop reactor and thereby the samples obtained fulfill the requirements of representatively. However, the method may not be applied, for example, in the sample take-out between two successive loop reactors. The in-line filter applied in the method is placed inside of a separate pipe, whereby the maintenance may be troublesome. The method is further based on that the flow velocity over the filter element must be considerably large in order to avoid plugging. In order to achieve a large flow velocity, the pressure difference over the loop pump must be sufficient. This limits the use of the method in smaller reactor. Further in certain operation conditions the flow velocity in the loop reactor may, however, be relatively low, which makes the available pressure difference lower. Likewise, under certain conditions the product suspension circulating in the loop reactor may contain relatively much of solids, whereby its circulating via a separate pipe may cause problems. Thus a need exist for further improvements in the sample take-out straight from the reaction medium.

OBJECTS AND SUMMARY OF THE INVENTION

Thus the object of the invention is a method and an apparatus for taking a sample straight from the loop reactor without time delay and without the adhering problems caused by polymer particles. Another object of the invention is a method and an apparatus of taking samples from a polymer suspension transferred from one reactor to another. Still further object of the invention is a method and an apparatus for taking sample from a polymer suspension coming out from a loop reactor.

The method according to the invention for taking a sample from a flowing suspension formed by polymer particles and hydrocarbon diluent in olefin polymerization is characterized in that it comprises taking the sample via at least one filter means situated at the plane of inside surface of flow space, and which filter means is furnished with such perforation, where the size of perforation is essentially smaller than the smallest particle size of the catalyst used in the polymerization.

In the apparatus according to the invention high flow rates are not necessary for preventing plugging. In the pilot-range tests it has been found that the method works even with flow rates below 1 m/s. Further the operability has been shown in small loop reactors, in which a method based on the pressure difference over pump has not worked. According to the normal practice, it could be expected that the smaller the pore size of the filter, the more easily it plugs because of polymer layers. However, it has been surprisingly found that by using a filter element of very small pore size placed at the plane of inside surface of flow space, the plugging can be almost totally avoided.

The pressure difference over the filtering element is very small, because the reaction mixture to be analyzed is liquid in both sides of filter surface. Therefore the flow inside the filter element is strongest away from the pores and thus it attends to flush the filter surface.

The perforation size of the filter element can be 0.1–10 $\mu$m, preferably between 0.2–1$\mu$. Thus the pore size is smaller than the catalyst particle size used in the polymerization. It is preferable to use ceramic filters.

There are various ways to place the filter means. One way is to place the filter means straight to the wall of the loop reactor, whereby a sample is taken out straight from the loop reactor. In this case, a space can exist back of the filter means, in which space the pressure difference compared to the pressure prevailing in the loop reactor is small.

Another way is to place-the filter according to the invention into the transfer pipe between two loop reactors. A third way is to place the filter means according to the invention into the discharge leg or into a pipe going therefrom. The product is taken out continuously from the reactor through the discharge leg continuously or periodically. When desired amount of product is taken out from the reactor, the liquid reaction medium gasifies immediately and goes approximately with the sound velocity towards the settling tank along with the polymer powder.

In the apparatus according to the invention a part of the liquid sample flow separated from the polymer suspension can be introduced after vaporizing pressure decrease in gas form to an analyzer, for example into a GC-analyzer. A wax separation vessel can be in communication with pressure reducer which vessel separates wax solved in liquid and separable from it after gasification. Otherwise this wax would plug sample take-out system. A reservoir, which contains catalytic mass for removing catalyst residues, can also be in the sample take-out flow.

BRIEF DESCRIPTION OF THE DRAWINGS

The invention is further illustrated by enclosed figures, in which.

DETAILED DESCRIPTION OF THE PREFERRED EMBODIMENTS

Figure 1:
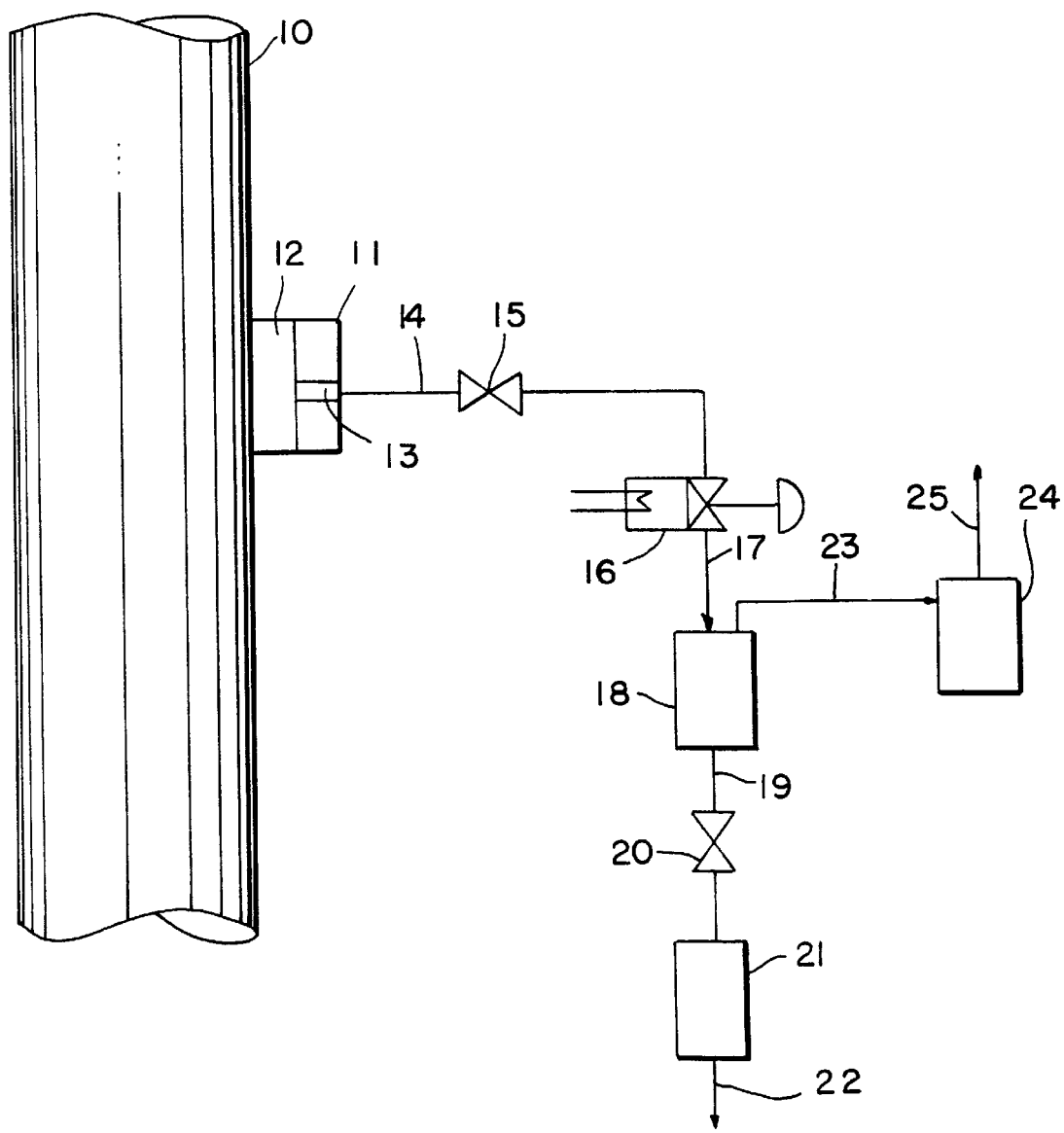
FIG. 1 illustrates the sample take-out according to the invention applied in one loop reactor.

In FIG. 1 a sample take-out system according to the invention is placed into a loop reactor 10. It comprises a filter means 12 and a pipe 13, which leads outside of the sample take-out means 11. The filter means 12 is furnished with a fine perforation of 0,5 $\mu$m and it is placed so, that the surface of filter means 12 opening into the loop reactor is at the plane of the inside surface of the reactor, i.e., flush therewith. Pipe 14 is introduced from the sample take-out system 11 equipped with a valve 15 further into a vaporizing pressure reducer 16. In the pressure reducer 16 the vaporized sample is introduced via the pipe 17 further into a wax separation vessel 18 and further via a pipe 19 into a wax removal vessel 21 through a value 20, from which the waxes can be removed from the system via a pipe 22.

A pipe 23 leads from the wax separation vessel 18 further to a removal reservoir 24 of catalyst residues and therefrom via a pipe 25 to a gas chromatograph for analysis.

Figure 2:
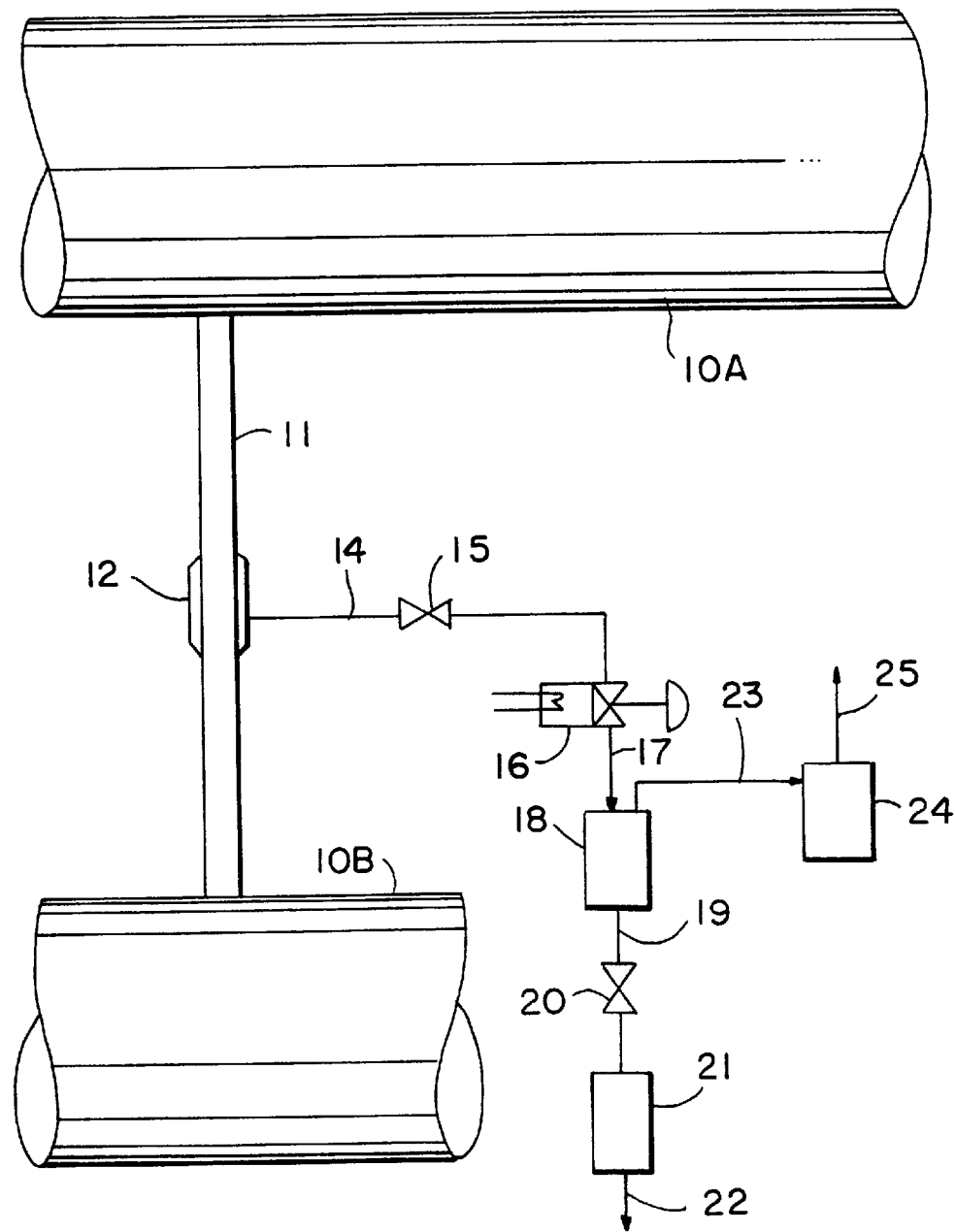
FIG. 2 illustrates the sample take-out system according to the invention placed between two loop reactors.

FIG. 2 discloses two loop reactors 10A and 10B connected by the pipe 11. In this case the sample take-out means are situated in the pipe 11. In this embodiment of the invention, hydrocarbon solvent contained in the suspension vaporizes within the transfer pipe 11 and, therefore, the suspension passing through the filter means is at least partially gaseous. Otherwise FIG. 2 is similar as FIG. 1.

EXAMPLES 1–4

A pilot scale apparatus according FIG. 1 was used for preparation of such homo and copolymers of ethylene, in which the melt index is high and/or the density is low, eg. products which are typically most difficult because of fines, solubility and wax forming problems. By using the sample take-out system according to the invention the analyzing succeeded reliably all the time.

The process conditions and the product properties are presented in the following table.

|  | Example 1 | Example 2 | Example 3 | Example 4 |
| --- | --- | --- | --- | --- |
| Reactor temperature ° C. | 60 | 75 | 60 | 70 |
| Hydrogen/ethylene ratio mol/kmol | 75 | 350 | — | 850 |
| Comonomer/ethylene ratio mol/kmol | 940 | 150 | — | 0 |
| MFR$_2$ of the product g/10 min | 17 | 350 | 11 | 1117 |
| Product density kg/m$^3$ |  |  | 922 |  |
| Flow rate of reaction mixture on the filtering means m/s | 0,3 | 0,3 | 0,3 | 0,3 |

EXAMPLE 5

Into a continuously operated polymerization reactor of 50 dm$^3$ 2.0 kg/h of ethylene, 360 g/h of 1-butene, 0.2 g/h of hydrogen, 14.0 g/h of catalyst and 28.0 kg/h of propylene were introduced. The temperature of the reactor was 60° C. The polymer slurry was introduced into another reactor in a transfer line, in which a filter means according to the invention having a perforation size of 0,5 $\mu$m was mounted. The sample from the filter was introduced first into a vaporizer, then into a wax separator and further into a gas chromatograph. The analyzed hydrogen/ethylene ratio was 55 mol/kmol and butene/ethylene ratio was 570 mol/kmol. In spite of very high butene/ethylene ratio the sample take-out worked well without plugging.

We claim:

1. A method for taking a sample from a flowing suspension of polymer particles and hydrocarbon diluent undergoing olefin polymerization using at least one catalyst, comprising the steps of:

arranging a flow space, comprising a product transfer pipe, in flow communication between at least two polymerization reactors, directing the suspension to flow through the flow space along a surface of the product transfer pipe, arranging a filter made of a material having pores flush with said surface of said product transfer pipe along which the suspension flows, and selecting the size of said pores of said filter to enable a portion of the suspension to flow through said filter and to prevent substantially any of the at least one catalyst from passing through said filter.

2. The method of claim 1, further comprising the step of: selecting the size of said pores of said filter to be in a range from about 0.1 µm to about 10 µm.

3. The method of claim 1, further comprising the step of: selecting the size of said pores of said filter to be in a range from about 0.2 µm to about 1 µm.

4. The method of claim 1, wherein said step of arranging said filter flush with said surface of said flow space comprises the step of arranging said filter in a middle portion of said surface such that the flow suspension flows along said surface both before and after said filter.

5. In an olefin polymerization arrangement including at least two polymerization reactors in which a flowing suspension of polymer particles and hydrocarbon diluent undergoes olefin polymerization using at least one catalyst and an apparatus for taking a sample from the suspension, the apparatus for taking the sample from the suspension comprising:

means defining a flow space through which the suspension is directed, said flow space comprising a product transfer pipe extending between and in fluid communication with said at least two polymerization reactors and having a surface along which the suspension flows, and at least one filter made of a material having pores arranged flush with said surface of said product transfer pipe along which the suspension flows, said pores having a certain size to enable a portion of the suspension to flow through said at least one filter and to prevent substantially any of the at least one catalyst from passing through said filter.

6. The arrangement of claim 5, wherein the size of said pores of said at least one filter is in a range from about 0.1 µm to about 10 µm.

7. The arrangement of claim 5, wherein the size of said pores of said at least one filter is in a range from about 0.2 µm to about 1 µm.

8. The arrangement of claim 5, wherein said means defining said flow space comprises a loop reactor pipe of the at least one polymerization reactor.

9. The arrangement of claim 5, wherein said means defining the flow space comprises a polymer transfer pipe in which hydrocarbon solvent in the suspension vaporizes, the suspension passing through said at least one filter thus being at least partially gaseous.

10. The apparatus as in claim 5, further comprising means for feeding the suspension from said flow space through said at least one filter.

11. The apparatus as in claim 5, further comprising a space located outside said flow space, wherein said filter is in flow communication with said space and wherein said space has a pressure difference which is less than the pressure of said flow space.

12. In an olefin polymerization arrangement including at least one polymerization reactor in which a flowing suspension of polymer particles and hydrocarbon diluent undergoes olefin polymerization using at least one catalyst and an apparatus for taking a sample from the suspension, the apparatus for taking the sample from the suspension comprising:

means defining a flow space through which the suspension is directed, said means including a surface along which the suspension flows, at least one filter made of a material having pores arranged flush with said surface along which the suspension flows, said pores having a certain size to enable a portion of the suspension to flow through said at least one filter and to prevent substantially any of the at least one catalyst from passing through said filter, and wherein said means defining the flow space comprises a polymer transfer pipe structured and arranged along with the at least one reactor such that hydrocarbon solvent in the suspension at least partially vaporizes and the suspension passing through said at least one filter is at least partially gaseous.

* * * * *